US006356787B1

(12) United States Patent
Rezai et al.

(10) Patent No.: US 6,356,787 B1
(45) Date of Patent: Mar. 12, 2002

(54) METHOD OF TREATING FACIAL BLUSHING BY ELECTRICAL STIMULATION OF THE SYMPATHETIC NERVE CHAIN

(75) Inventors: Ali R. Rezai; Martin Zonenshayn, both of New York City, NY (US)

(73) Assignee: Electro Core Techniques, LLC, Summit, NJ (US)

( * ) Notice: Subject to any disclaimer, the term of this patent is extended or adjusted under 35 U.S.C. 154(b) by 0 days.

(21) Appl. No.: 09/511,841

(22) Filed: Feb. 24, 2000

(51) Int. Cl.[7] ................................................. A61N 1/32
(52) U.S. Cl. ........................................................ 607/45
(58) Field of Search ........................... 607/1, 2, 45, 48, 607/63, 72

(56) References Cited

U.S. PATENT DOCUMENTS 6,073,048 A * 6/2000 Kieval et al. ................. 607/17

* cited by examiner

Primary Examiner—George R. Evanisko
(74) Attorney, Agent, or Firm—Joseph P. Errico; Timothy J. Bortree

(57) ABSTRACT

A method for treating excessive facial blushing by applying an oscillating electric field to the stellate ganglion. The method includes the steps of inserting an electrode into the vacinity of the sympathetic ganglion, for example the stellate ganglion, such that the necessary electric field may be applied to the ganglion. The necessary field oscillation frequency and strength, as well as other characteristics of the signal are determined individually for each patient. Continued driving of the pathological activity of the ganglion into the normal function is the long-term, reversible palatative remedy for the condition.

3 Claims, 2 Drawing Sheets

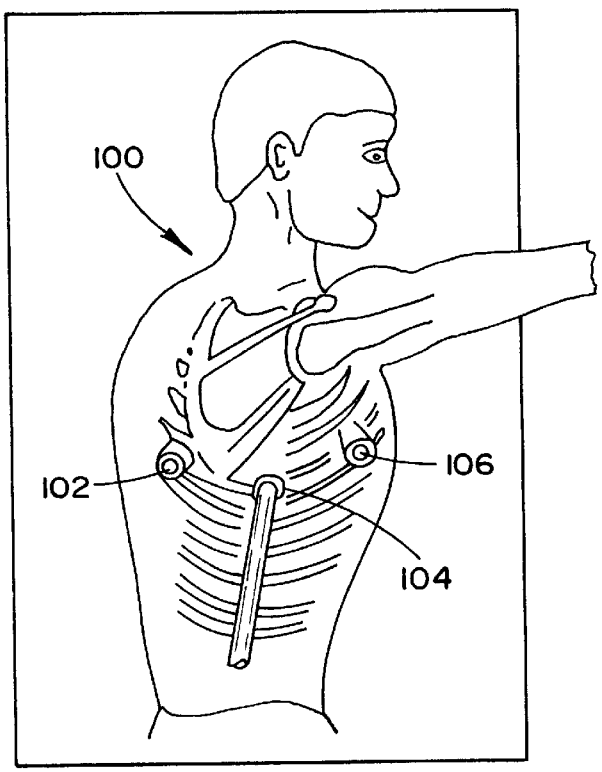
FIG. 1
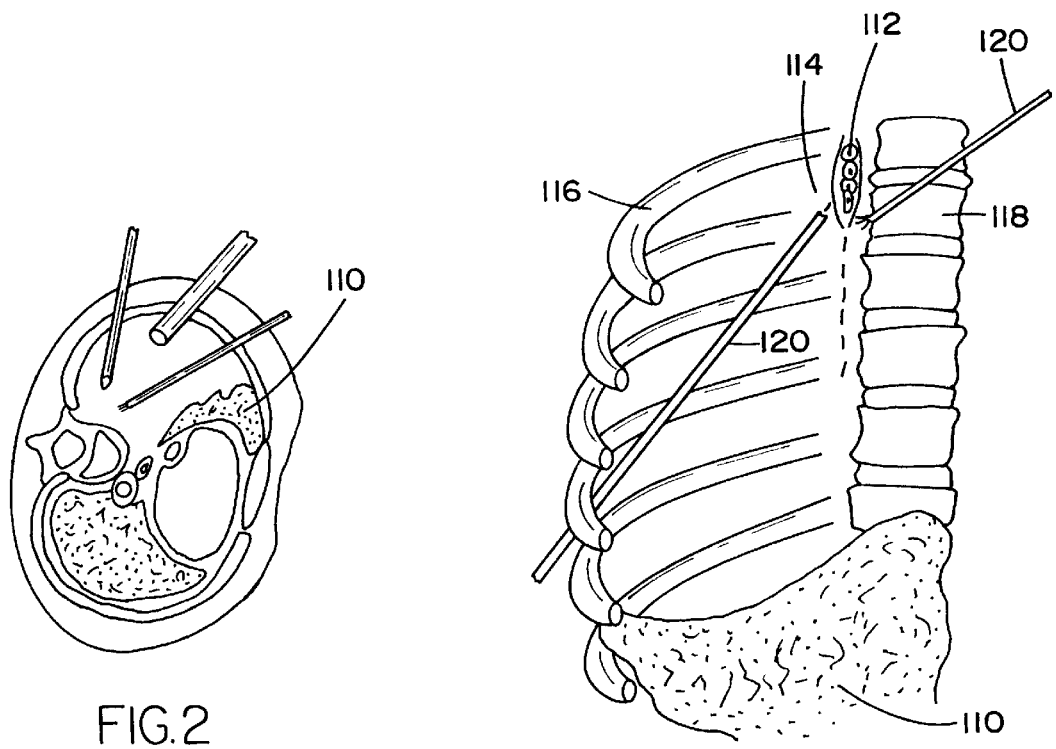
FIG. 2
FIG. 3

METHOD OF TREATING FACIAL BLUSHING BY ELECTRICAL STIMULATION OF THE SYMPATHETIC NERVE CHAIN

BACKGROUND OF THE INVENTION

1. Field of the Invention

This invention relates generally to the treatment of a disorder known as facial blushing, or excessive redness of the face elicited by emotional or social stimuli, by the electrical stimulation of the corresponding cluster of nerves and/or ganglia in the sympathetic chain and more specifically, for example, stimulation of the inferior cervicothoracic (stellate) down to the second and/or third thoracic ganglia is employed to treat facial blushing.

2. Description of the Prior Art

Within the field of neurosurgery, the use of electrical stimulation for the treatment of pathologies, including such disorders as uncontrolled movement, such as Parkinson's disease and essential tremor, as well as chronic pain and eating disorders, has been widely discussed in the literature. It has been recognized that electrical stimulation holds significant advantages over alternative methods of treatment, for example lesioning, inasmuch as successful lesioning destroys all nerve activity. Collateral damage to non-targeted tissues is also a significant risk in lesioning treatments. In many instances, it is, therefore, the preferred effect is to stimulate or reversibly block nervous tissue. Electrical stimulation permits such stimulation of the target neural structures, and equally importantly, it does not require the destruction of the nervous tissue (it is a reversible process, which can literally be shut off or removed at will). In addition, stimulation parameters can be adjusted so that benefits are maximized, and side effects are minimized.

The particular application which the present invention is directed to, is the treatment of facial and neck blushing. The principle symptom of this disorder is excessive and frequent redness of the face which is easily elicited by emotional or social stimuli. The instantaneous appearance of blushing is produced by normal events in daily life such as eating with other people, meeting someone, shopping, speaking in public, an so on. The disorder can be quite pronounced, and it effects a significant percentage of people who suffer from social phobia. The prevalence rate of social phobia is approximately 10%, or 30 million people in the United Sates alone. While many in the medical community consider facial blushing trivial or normal, many patients, in fact, state that it causes a significant negative impact on their quality of life. In a recent study of 244 patients undergoing ablative surgery for this disorder, 17% of patients were forced to take periodic sick leave or early retirement. Suicide was considered among a quarter of patients, while half of patients used alcohol as a means of relieving their facial blushing.

Normal blushing of skin, and in particular, the face, is a reflection of the vasodilatory effects of blood vessels in the skin caused by emotional stimuli. This effect is mediated by the sympathetic nervous system originating in the upper thoracic portion of the sympathetic chain. The cause of the condition is a dysfunction in the nerve cluster known as the cervicothoracic (lower stellate and upper thoracic) ganglia, which is one of the sequence of nerve clusters extending along the outside of the spinal column, and forms the sympathetic nervous system. The sympathetic, along with the parasympathetic, nervous system is part of the autonomic, or vegetative, nervous system. The effects of the autonomic system are extensive, and range from the control of blood pressure, heart rate, sweat, and body heat, to blood glucose levels, sexual arousal, and digestion. With respect to the current embodiment, the sympathetic outflow to the faces originate in the lower portion of the stellate, and the first 2–3 thoracic ganglia. These peripheral nerve fibers synapse, or converge, in small nodes of nerve cells, called ganglia which lie alongside the vertebral bodies in the neck, chest, and abdomen. In particular, the stellate ganglion is located laterally adjacent to the intervertebral space between the seventh cervical and first thoracic vertebrae. The first, second, and third thoracic ganglia lie next to their respective vertebral bodies on either side of the thoracic cavity. In patients suffering from facial blushing, it is these ganglia which play a major role in the abnormal signal generation to the blood vessels of the face and neck. There is presently no effective medicinal treatment for the condition. In the aforementioned study, 22% of patients had tried medications called beta-blockers with minimal or no relief. Many patients also undergo expensive psychological treatments, such as cognitive and behavioral therapies, without significant relief of symptoms. The present standard of care for the interventional treatment of facial blushing is the lesioning of the stellate and upper thoracic ganglia via one of several surgical approaches.

While there are a variety of different techniques and mechanisms which have been designed to focus the lesioning means directly onto the target nerve tissue, collateral damage is inevitable. Were it even possible to direct all lesioning energy onto the target nerve cluster, it is a significant drawback that other functioning of these nerves is lost, even when such functioning may not be pathological. In addition, there are several common side effects described in the medical literature, including an ipsilateral Horner's syndrome (drooping eyelid and smaller pupil), compensatory sweating (increased sweating in other areas), and gustatory sweating (sweating, particularly of the face, at the smell of certain foods). Additionally, many patients suffer a variety of side effects from medications such as beta blockers, including lethargy, hallucinations, nausea, diarrhea, impotence, hypoglycemia without the normally accompanying tachycardia, fever, and arthralgias.

These complications can be minimized to a large extent, or possible eliminated, by the use of chronic electrical stimulation or continuous drug infusion. The reasons are many, and include the possibility of changing which contacts of a multipolar lead are stimulated to minimize stimulating the superior portion of the stellate ganglion which can lead to a Horner's syndrome, to adjusting the parameters such as frequency or pulse width to affect changes in compensatory and gustatory sweating, should they arise.

It is therefore the principle object of the present invention to provide a less destructive and fully reversible and adjustable method of treating facial blushing.

SUMMARY OF THE INVENTION

The preceding objects are provided in the present invention, which comprises new and novel methods of treating facial blushing disorders by implantation of stimulation electrodes at specific locations along the sympathetic chain. More particularly the present invention comprises a method of therapeutically treating facial and cervical blushing by surgically implanting an electrode adjacent to a predetermined site along the sympathetic chain on the affected side of the body, or if clinically indicated, bilaterally. This involves the surgical implantation of a stimulating electrode over the inferior portion of the stellate ganglion, and usually over T2-3. The most commonly employed surgical approach is aided by video-assisted thoracoscopy, which involves the placement of 2–4 small incisions or ports in the chest wall, through which instruments may traverse en route to the lateral aspect of the vertebral bodies where the sympathic chain lies extrapleurally. The distal end of the lead can be secured to surrounding tissues and be placed either directly over the sympathetic chain or over the internal aspect of the parietal pleura. The proximal end of the lead can be passed out of the thoracic cavity via one of the neighboring surgical ports, and tunneled subcutaneously to an electrical signal source which, in turn, is operated to stimulate the predetermined treatment site over the sympathetic ganglia, such that the clinical effects of the facial blushing disorder are reduced with minimal side effects.

Alternatively, a catheter with either end- or side-apertures placed over the ganglia of interest is connected in a similar fashion to a infusion pump. In addition, this embodiment is extended to include a combination electrical contact and drug delivery system, as well as a system which has the capacity to sense or record electrical or chemical activity in the region of interest.

BRIEF DESCRIPTION OF THE DRAWINGS

FIG. 1 is a schematic illustration of a patient lying in the lateral decubitus position having one visualization port in the fifth intercostal space at the mid-axillary line and two instrument ports at the fourth and fifth intercostal space at the anterior and posterior axillary lines, respectively;

FIG. 2 is an axial cross section view of the upper thoracic region including one visualization port and two instrument ports wherein the two instrument ports have disposed therethrough endoscopic instruments accessing the ipsilateral paravertebral region where the sympathetic chain lies;

FIG. 3 is an exposed view of the left hemithorax displaying one instrument tenting the parietal pleura while the second endoscopic instrument is incising the parietal pleura to expose the sympathetic chain.

DETAILED DESCRIPTION OF THE PREFERRED EMBODIMENT

Figure 4:
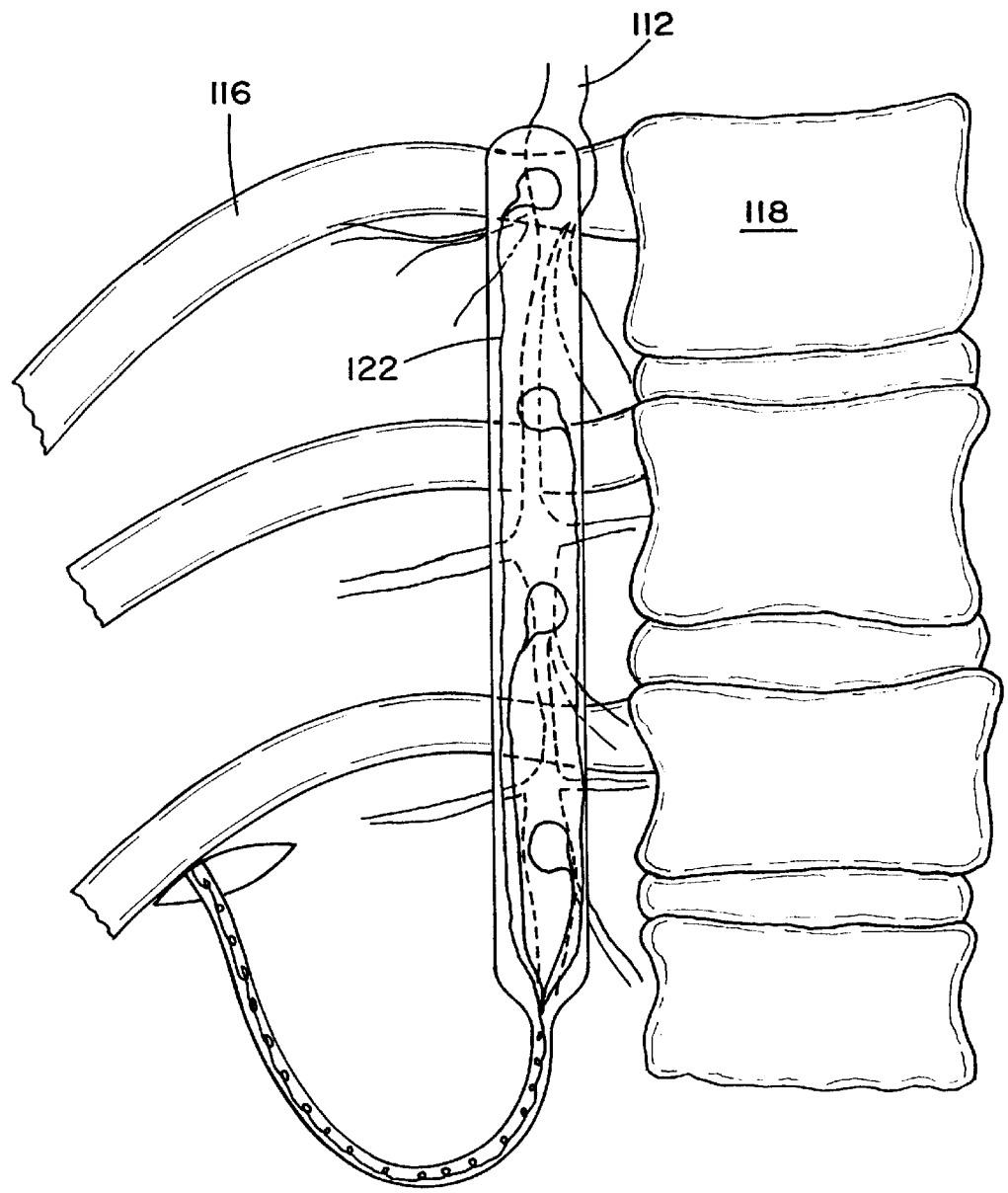
FIG. 4 is a side view of an exposed superior thoracic ganglia in which an electrical stimulation lead is disposed adjacent thereto.

There are many several approaches described in the literature that have been employed in the lesioning of the stellate and superior thoracic sympathetic ganglia. With respect to this embodiment, any one or a combination of these methods, as well as modifications of this technique not herein described, may be possible without deviating from the broad spirit and principle of the present invention. Specifically, it will be apparent to those skilled in the art that variations and modifications are possible without deviating the scope of the current embodiment which describes the technique of changing the functional state of the upper thoracic and cervicothoracic (stellate) sympathetic ganglia via chronic electrical stimulation or infusion of drug known to modulate its function.

Referring now to FIG. 1, in which a patient 100 is illustrated in the decubitus position, having been prepared by the surgical insertion of three ports 102,104,106 into the left hemithorax. This preparation is anticipation of a thoracoscopic approach, which is a typical and feasible surgical technique utilized for lesioning of these ganglia. More specifically, this approach commonly involves positioning the patient in the lateral decubitus position, with the hips below the flexion joint of the operating room table. Subsequent flexion of the table allows some separation of the ribs by dropping the patient's hips and therefore increasing the intercostal space to work through. The ipsilateral arm is abducted on an arm holder. Rotating the table somewhat anteriorly and using reverse Trendelenburg positioning further maximizes the exposure to the superior paravertebral area by allowing the deflated lung (see FIGS. 2 and 3) to fall away from the apical posterior chest wall. The patient is under placed under general anesthesia and intubated via a double lumen endotracheal tube. This allows for ventilation of one lung, and collapse of the lung on the side to be operated upon without using carbon dioxide insufflation. Three 2 cm incisions for the thoracoscopic sympathectomy are ordinarily used. One incision is in the midaxillary line in the fifth intercostal space and is used as the telescopic video port 104. The second incision, performed under endoscopic observation, is placed in the third or fourth intercostal space at the anterior axillary line and is used as one of two instrument channels 106. The third incision is made at the posterior axillary line just below the scapular tip in the fifth interspace, and it is used as the second instrument channels 102. Additional incisions/ports can be made as necessary.

Referring now also to FIGS. 2 and 3, in which axial cross section and exposed views of the surgical field are provided, respectively, the surgical exposure and preparation of the relevant portion of the sympathetic chain for the treatment of facial blushing is described. After the lung 110 is collapsed, and if necessary, retracted down by a fanning instrument via one of the working ports, the sympathetic chain 112 is visualized under the parietal pleura 114 as a raised longitudinal structure located at the junction of the ribs 116 and the vertebral bodies 118. The parietal pleura 114 is grasped between the first and second ribs in the region overlying the sympathetic chain 112 and the endoscopic cautery or scissors 120 is used to incise the pleura 114 in a vertical manner just below the first rib thereby exposing the sympathetic chain 112.

Referring now also to FIG. 4, in which the placement of the multichannel electrode adjacent to the symnpathetic chain is shown, the implantation of the stimulation electrode is now described. Once the sympathetic chain 112 has been exposed, a multipolar electrode 122 is placed over sympathetic chain of interest, typically the inferior third of the stellate ganglion to the T2 ganglion, and sutured in place to the nearby tissue or parietal pleura 114.

Alternatively one may prefer not to incise the parietal pleura 114 if electrical stimulation is used, as the current which is generated may modulate the functioning of the ganglia through the pleural surface. Pending the preference and comfort level of the surgeon, a temperature probe may be placed on the ipsilateral face, and electrical stimulation (or in the case of the alternate drug infusion embodiment) testing may be performed prior to closure of the chest cavity to maximize the probability of future effective therapy. The temperature should rise during high frequency stimulation.

This procedure can most easily be accomplished by using existing electrode configurations, or modifications thereof, with the distal tip being more superior, and the proximal tip and the connection cable being more inferior. The lead can be inserted into the thoracic cavity and held in place via the posterior axillary line incision and sutured by using the other working port. The proximal connecting cable can be left at the posterior axillary line port after the lead has been secured with some remaining "slack" of connecting sable being left in the inter-pleural space. The proximal end of the connecting cable/tube can be brought out of the thoracic cavity, and via an extension cable/tube, be tunneled subcutaneously and connected to an electrical pulse generator or infusing pump. The pulse generator or pump may be placed in the subcutaneous tissues of the flank area, abdominal wall area, or buttock area, etc. Any excess fluid is suctioned from the thoracic cavity and the lung is reinflated. A suctioning chest tube may or may not be used depending on the presence or absence of damage to the visceral pleura of the lung. The incisions are closed, and a chest X-Ray is obtained in the recovery room to ensure the lung has reinflated. Electrical stimulation or drug infusion therapy may be started immediately, or after a delay, allowing for some healing to occur first.

Alternative approaches include posterior open extrapleural techniques, posterior percutaneous approaches, the anterior supraclavicular method, as well as the open transthoracic approach. However, while there has been described and illustrated specific embodiments of new and novel methods of treatment for facial and cervical blushing, and it will be apparent to those skilled in the art that variations and modifications are possible, such alterations shall be understood to be within the broad spirit and principle of the present invention which shall be limited solely by the scope of the claims appended hereto.

We claim:

1. A method of interventionally and reversibly treating excessive blushing conditions comprising:

positioning at least one electrode, having distal and proximal termini, such that the distal terminus is in the vicinity of the sympathetic chain;

coupling the proximal terminus of the at least one electrode to an electrical signal source;

applying an oscillating electric field to the sympathetic chain until the symptoms of the excessive blushing condition have been demonstrably alleviated; and continuing the application of the oscillating electric field.

2. The method as set forth in claim 1, wherein the vacinity of the sympathetic chain is adjacent to the stellate ganglion.

3. The method as set forth in claim 1, wherein the at least one electrode is a multipolar electrode and the application of the oscillating electric field is multipolar.

* * * * *